(12) United States Patent
Kobayashi

(10) Patent No.: US 10,570,314 B2
(45) Date of Patent: Feb. 25, 2020

(54) POLISHING AGENT, POLISHING METHOD, AND LIQUID ADDITIVE FOR POLISHING

(71) Applicant: AGC Inc., Chiyoda-ku (JP)

(72) Inventor: Genki Kobayashi, Tokyo (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/700,480

(22) Filed: Sep. 11, 2017

(65) Prior Publication Data

US 2018/0072917 A1    Mar. 15, 2018

(30) Foreign Application Priority Data

Sep. 13, 2016  (JP) .................. 2016-178507

(51) Int. Cl.
| | | |
|---|---|---|
| *C09G 1/02* | (2006.01) | |
| *C09G 1/16* | (2006.01) | |
| *H01L 21/321* | (2006.01) | |
| *C01B 13/00* | (2006.01) | |
| *C07D 521/00* | (2006.01) | |
| *C08L 71/02* | (2006.01) | |

(52) U.S. Cl.
CPC ............ *C09G 1/02* (2013.01); *C09G 1/16* (2013.01); *H01L 21/3212* (2013.01); *C01B 13/00* (2013.01); *C07D 521/00* (2013.01); *C08L 71/02* (2013.01)

(58) Field of Classification Search
CPC .................................................. C09G 1/02
See application file for complete search history.

(56) References Cited

U.S. PATENT DOCUMENTS

| | | | |
|---|---|---|---|
| 6,569,216 B1 | 5/2003 | Taira et al. | |
| 2004/0065022 A1* | 4/2004 | Machii ............ | C09G 1/02 51/309 |
| 2004/0092103 A1 | 5/2004 | Fujii et al. | |
| 2006/0124026 A1* | 6/2006 | Kollodge .......... | C09G 1/02 106/3 |
| 2006/0214133 A1* | 9/2006 | Yamashita ........ | C09G 1/02 252/186.1 |
| 2009/0197415 A1 | 8/2009 | Fujii et al. | |
| 2012/0100718 A1* | 4/2012 | Minami ............ | C09G 1/02 438/693 |
| 2013/0203254 A1* | 8/2013 | Tamada ........... | B24B 37/044 438/692 |
| 2015/0159049 A1* | 6/2015 | Amano ............. | C09G 1/02 438/693 |
| 2016/0108284 A1* | 4/2016 | Yoshizaki ......... | C09K 3/1463 252/79.1 |

(Continued)

FOREIGN PATENT DOCUMENTS

| | | |
|---|---|---|
| JP | 2000-160142 | 6/2000 |
| JP | 2006-278773 | 10/2006 |

(Continued)

*Primary Examiner* — Shuangyi Abu Ali
(74) *Attorney, Agent, or Firm* — Oblon, McClelland, Maier & Neustadt, L.L.P.

(57) ABSTRACT

The present invention relates to a polishing agent including: metal oxide particles; an organic acid having a monodentate ligand; a nonionic polymer; and water, in which the polishing agent has a pH of from 3.0 to 7.0, and the nonionic polymer includes at least one selected from the group consisting of polyglycerin, polyoxyethylene polyglyceryl ether and polyoxypropylene polyglyceryl ether.

15 Claims, 2 Drawing Sheets

(56) References Cited

U.S. PATENT DOCUMENTS

2017/0081552 A1* 3/2017 Yamato ................ C09K 3/1463
2017/0243752 A1* 8/2017 Yasui ....................... C09G 1/02

FOREIGN PATENT DOCUMENTS

| JP | 2015-120846 A | 7/2015 |
| JP | 2015-205348 A | 11/2015 |
| WO | WO 2013/125445 A1 | 8/2013 |
| WO | WO2014185285 * | 11/2014 |

* cited by examiner

POLISHING AGENT, POLISHING METHOD, AND LIQUID ADDITIVE FOR POLISHING

FIELD OF THE INVENTION

The present invention relates to a polishing agent, a polishing method, and a liquid additive for polishing. Particularly, the present invention relates to a polishing agent for chemical mechanical polishing in the manufacturing of a semiconductor integrated circuit, a polishing method using the polishing agent, and a liquid additive for polishing, for preparing a polishing agent.

BACKGROUND OF THE INVENTION

In recent years, with high integration and high functionality of a semiconductor integrated circuit, the development of microfabrication technology for miniaturization and density growth of a semiconductor element is advancing. In the manufacturing of a semiconductor integrated circuit device (hereinafter also referred to as a "semiconductor device"), in order to prevent the problem such that unevenness (difference in level) of the surface of a layer exceeds depth of focus of lithography and sufficient resolution is not obtained, it is conventionally performed to flatten an interlayer insulating film, an embedding wiring and the like using chemical mechanical polishing (hereinafter referred to as "CMP"). Importance of high flattening by CMP is increasing with severer requirements of high definition and miniaturization of an element.

Furthermore, in recent years, in the manufacturing of a semiconductor device, an isolation method by shallow trench having small element isolation width (Shallow Trench Isolation; hereinafter referred to as "STI") is introduced in order to proceed with higher miniaturization of a semiconductor element.

The STI is a technique for forming an electrically insulated element region by forming a trench (groove) on a silicon substrate and embedding an insulating film in the trench. In the STI, as shown in FIG. 1A, an element region of a silicon substrate 1 is masked with a silicon nitride film 2 or the like, a trench 3 is formed on the silicon substrate 1, and an insulating layer such as a silicon dioxide film 4 is then deposited so as to embed the trench 3. The silicon dioxide film 4 on the silicon nitride film 2 as a convex part is polished and removed by CMP while remaining the silicon dioxide film 4 in the trench 3 as a concave part. Thus, an element isolation structure having the silicon dioxide film 4 embedded in the trench 3 is obtained as shown in FIG. 1B.

In CMP in the STI, the progress of polishing can be stopped at the time of exposure of a silicon nitride film by increasing a selection ratio between a silicon dioxide film and a silicon nitride film (the selection ratio means a ratio between a removal rate of the silicon dioxide film and a removal rate of the silicon nitride film, and is hereinafter referred to as a "selection ratio" for simplicity). Thus, a polishing method using the silicon nitride film as a stopper film can obtain smoother surface as compared with the conventional polishing method.

Thus, in CMP technology in recent years, not only high removal rate to a silicon dioxide film is required, but also the high selection ratio is important, from the standpoint of cost.

In view of the above, a method for improving polishing characteristics of a polishing agent in conformity with the required characteristics is proposed. Patent Document 1 discloses a polishing agent for a hard disk substrate or a semiconductor substrate, containing cerium oxide particles and the like as abrasives for polishing, and containing an organic acid having a multidentate ligand, and a polyhydric alcohol compound or its derivative.

The polishing agent disclosed in each of Patent Document 1 and Patent Document 2 can secure a removal rate of high value to some extent, but suppression of a removal rate to a silicon nitride film is not sufficient. Therefore, it was not said that the selection ratio between a silicon dioxide film and a silicon nitride film is sufficiently high.

Patent Document 1: JP-A-2000-160142
Patent Document 2: JP-A-2006-278773

SUMMARY OF THE INVENTION

The present invention has been made to solve the above-described problems, and has an object to provide a polishing agent, a polishing method and a liquid additive for polishing in which a removal rate to a silicon nitride film is suppressed low while maintaining sufficiently high removal rate to a silicon oxide film such as a silicon dioxide film, for example, in CMP, particularly CMP of a surface to be polished which includes a surface including silicon oxide in STI, thereby being able to achieve high selection ratio and satisfactory flatness.

A polishing agent of the present invention is a polishing agent including: metal oxide particles; an organic acid having a monodentate ligand; a nonionic polymer; and water, in which the polishing agent has a pH of from 3.0 to 7.0, and the nonionic polymer includes at least one selected from the group consisting of polyglycerin, polyoxyethylene polyglyceryl ether and polyoxypropylene polyglyceryl ether.

In the polishing agent of the present invention, it is preferable that the organic acid having a monodentate ligand is at least one selected from the group consisting of monocarboxylic acid having a heterocycle, monocarboxylic acid having 4 or more carbon atoms and having a hydroxyl group, and monocarboxylic acid having an amino group. It is preferable that the metal oxide particles are cerium oxide particles.

It is preferable that the organic acid having a monodentate ligand is contained in an amount of from 0.003 to 1.0 mass % based on a total mass of the polishing agent. It is preferable that the nonionic polymer is contained in an amount of from 0.0002 to 2.0 mass % based on the total mass of the polishing agent. It is preferable that the metal oxide particles have an average secondary particle size of from 10 nm to 500 nm. It is preferable that the metal oxide particles are contained in an amount of from 0.01 to 10.0 mass % based on the total mass of the polishing agent.

A polishing method of the present invention is a polishing method including bringing a polishing pad into contact with a surface to be polished while supplying a polishing agent to perform polishing by relative movement therebetween, in which the surface to be polished including a surface including silicon oxide of a semiconductor substrate is polished using the polishing agent according to the present invention as the polishing agent.

A liquid additive for polishing of the present invention is a liquid additive for preparing a polishing agent by mixing with a dispersion of metal oxide particles, including: an organic acid having a monodentate ligand; a nonionic polymer; and water, in which the liquid additive has a pH of from 3.0 to 7.0 and the nonionic polymer includes at least one selected from the group consisting of polyglycerin, polyoxyethylene polyglyceryl ether and polyoxypropylene polyglyceryl ether.

In the liquid additive for polishing of the present invention, it is preferable that the organic acid having a monodentate ligand is at least one selected from the group consisting of monocarboxylic acid having a heterocycle, monocarboxylic acid having 4 or more carbon atoms and having a hydroxyl group, and monocarboxylic acid having an amino group.

In the present invention, the term "surface to be polished" is a surface to be polished of an object to be polished, and means, for example, the surface. In the present specification, a surface in an intermediate stage appearing on a semiconductor substrate in the process of manufacturing a semiconductor device is also included in the "surface to be polished".

In the present invention, "silicon oxide" is specifically silicon dioxide, but the invention is not limited to only silicon dioxide, and includes silicon oxide other than silicon dioxide.

According to the polishing agent and the polishing method of the present invention, a removal rate to a silicon nitride film is suppressed low and high selection ratio between silicon oxide film and silicon nitride film can be achieved, while maintaining sufficiently high removal rate to a silicon oxide film, for example, in CMP, particularly CMP of a surface to be polished which includes a surface including silicon oxide in STI.

DETAILED DESCRIPTION OF THE INVENTION

Figure 1A:
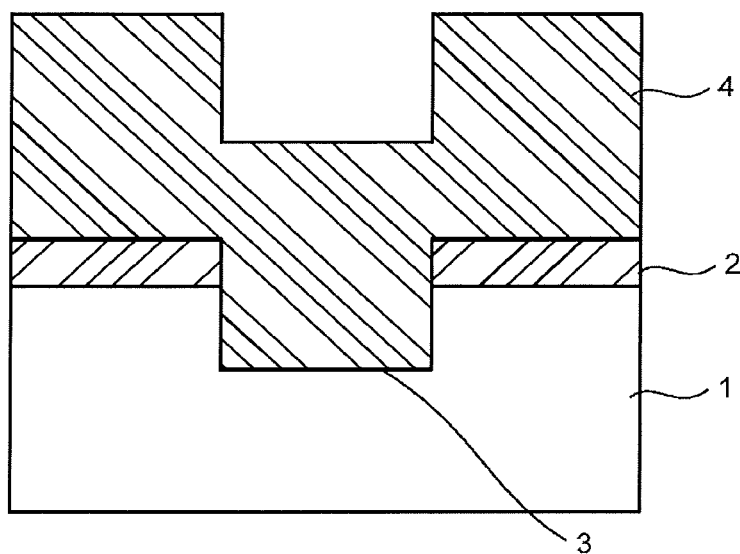
FIGS. 1A and 1B are cross-sectional views of a semiconductor substrate showing a polishing method by CMP in STI.
Figure 1B:
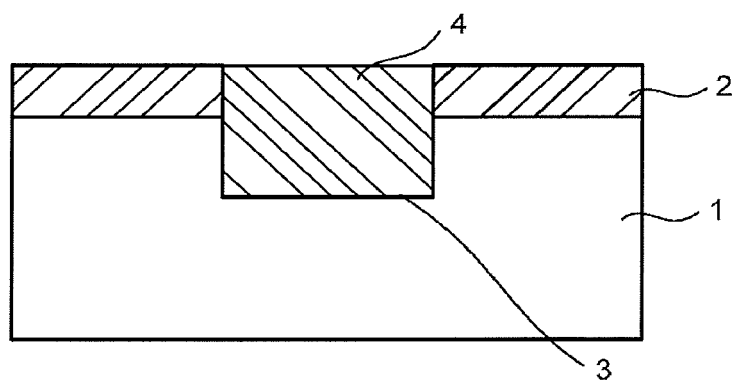

An embodiment of the present invention is described below. However, the present invention is not limited to the following embodiment, and other embodiments can be included in the scope of the present invention so long as those conform to the gist of the present invention.

Polishing Agent

The polishing agent of the present invention is a polishing agent including metal oxide particles, an organic acid having a monodentate ligand, a nonionic polymer and water, and having a pH of from 3.0 to 7.0, in which the nonionic polymer includes at least one selected from the group consisting of polyglycerin, polyoxyethylene polyglyceryl ether and polyoxypropylene polyglyceryl ether. The nonionic polymer including at least one selected from the group consisting of polyglycerin, polyoxyethylene polyglyceryl ether and polyoxypropylene polyglyceryl ether is hereinafter referred as a nonionic polymer (P).

When the polishing agent of the present invention is used in, for example, CMP of a surface to be polished which includes a silicon oxide film (for example, a silicon dioxide film) in STI, the polishing agent has high removal rate to the silicon oxide film, and in addition to this, a removal rate to a silicon nitride film is sufficiently low, and high selection ratio between the silicon oxide film and the silicon nitride film can be achieved. Furthermore, polishing having high flatness can be realized.

The mechanism that the polishing agent of the present invention exhibits such excellent polishing characteristics is not clear, but it is considered to be due to that the polishing agent contains both an organic acid having a monodentate ligand and a nonionic polymer (P) having specific molecular structure. That is, it is considered to be due to that the organic acid having a monodentate ligand contained in the polishing agent is electrostatically adsorbed on the surface of the metal oxide particles and the surface to be polished including the silicon oxide film through terminal groups of the respective molecules in the pH region of from 3.0 to 7.0 in the presence of the nonionic polymer (P) having the specific molecular structure. It is considered that the state of the surface of the metal oxide particles and the surface to be polished including the silicon oxide film is optimized, and as a result, both high polishing rate to the silicon oxide film and high selection ratio between the silicon oxide film and the silicon nitride film can be achieved without impairing dispersibility of the metal oxide particles.

Each component contained in the polishing agent of the present invention and a pH thereof are describe below.

Metal Oxide Particles

The metal oxide particles contained in the polishing agent of the present invention have a function as abrasives for polishing. Examples of the metal oxide particles include particles of metal oxides such as cerium oxide, aluminum oxide, silicon dioxide, titanium oxide and zirconium oxide. Of those, cerium oxide particles are preferred as the metal oxide particles since the removal rate to the silicon oxide film is high.

When the cerium oxide particles are used as the metal oxide particles in the polishing agent of the present invention, the cerium oxide particles contained in the polishing agent are not particularly limited, but cerium oxide particles produced by the method described in, for example, JP-A-11-12561 or JP-A-2001-35818 can be used. Specifically, in the present invention, cerium oxide particles can be used, which are obtained by adding an alkali to a cerium nitrate (IV) ammonium aqueous solution to prepare a cerium hydroxide gel, followed by filtering, cleaning and calcining, or cerium oxide particles obtained by pulverizing high purity cerium carbonate, and then calcining, followed by further pulverizing and classifying. Cerium oxide particles obtained by chemically oxidizing cerium (III) salt in a liquid, as described in JP-T-2010-505735, also can be used.

The metal oxide particles have an average particle size of preferably from 10 nm to 500 nm, and more preferably from 30 nm to 300 nm. In case where the average particle size thereof exceeds 500 nm, polishing flaws such as scratches are likely to be generated on the surface to be polished. On the other hand, in case where the average particle size thereof is less than 10 nm or less, removal rate is likely to be decreased. Additionally, since a percentage of a surface area per unit area is large, influence of surface state is easy to be received, and metal oxide particles become easy to aggregate depending on the conditions such as a pH and a concentration of an additive.

The metal oxide particles such as cerium oxide particles are present as aggregates (secondary particles) in which primary particles have been aggregated in a polishing agent. Therefore, the preferred average particle size of the metal oxide particles is represented by an average secondary particle size. Specifically, the metal oxide particles have an average secondary particle size of preferably from 10 nm to 500 nm, and more preferably 30 nm to 300 nm. The average secondary particle size is measured with a particle size analyzer of laser diffraction/scattering type or the like using a dispersion having particles dispersed in a dispersion medium such as pure water.

The content ratio (concentration) of the metal oxide particles is preferably from 0.01 to 10 mass % based on the total mass of the polishing agent. When the content ratio of the metal oxide particles is from 0.01 to 10 mass %, sufficiently high removal rate to a silicon oxide film can be obtained. Additionally, since a viscosity of the polishing agent is not so high, handling properties are satisfactory. The content ratio (concentration) of the metal oxide particles is more preferably from 0.025 to 3.0 mass %, and particularly preferably 0.025 to 1.0 mass %.

Metal oxide particles in the state of previously being dispersed in a medium (hereinafter referred to as "metal oxide particle dispersion") may be used as the metal oxide particles of the present invention. In such a case, water can be preferably used as the medium.

Water

The polishing agent of the present invention contains water as a medium for dispersing metal oxide particles and for dissolving an organic acid having a monodentate ligand and nonionic polymer (P) described hereinafter. The kind of water is not particularly limited, but considering the influence to the organic acid having a monodentate ligand and nonionic polymer (P), prevention of contamination by impurities, the influence to pH and the like, pure water, ultrapure water, ion-exchanged water and the like are preferably used.

Organic Acid Having Monodentate Ligand

The organic acid having a monodentate ligand contained in the polishing agent of the present invention is preferably monocarboxylic acid. The monocarboxylic acid is preferably at least one selected from monocarboxylic acid having a heterocycle, monocarboxylic acid having 4 or more carbon atoms and having a hydroxyl group, and monocarboxylic acid having an amino group. Examples of the monocarboxylic acid that is preferably used in the polishing agent of the present invention are described below, but the monocarboxylic acid is not limited thereto.

The monocarboxylic acid having a heterocycle that can be preferably used is monocarboxylic acid having a heterocycle containing a nitrogen atom (nitrogen-containing heterocycle), or monocarboxylic acid having a heterocycle containing a heteroatom other than nitrogen. Examples of the monocarboxylic acid having a heterocycle containing a nitrogen atom (nitrogen-containing heterocycle) include 2-pyridinecarboxylic acid, 3-pyridinecarboxylic acid, 4-pyridinecarboxylic acid, lysinecarboxylic acid, pyradinecarboxylic acid, 2-quinolinecarboxylic acid (quinaldinic acid), pyrrolidonecarboxylic acid, DL-pyroglutamic acid and DL-pipecolic acid.

The monocarboxylic acid having a heterocycle containing a heteroatom other than nitrogen includes monocarboxylic acid having a heterocycle containing only an oxygen atom as a heteroatom, and specific examples thereof include 2-furancarboxylic acid, 3-furancarboxylic acid and tetrahydrofuran-2-carboxylic acid.

The monocarboxylic acid having 4 or more carbon atoms and having a hydroxyl group preferably has 4 to 10 carbon atoms. Specific examples of such a monocarboxylic acid include salicyclic acid, 2-hydroxyisobutyric acid, glyceric acid, 2,2-bis(hydroxymethyl)propionic acid, 2,2-bis(hydroxymethyl)butyric acid, hydroxypivalic acid and malic acid.

Examples of the monocarboxylic acid having an amino group (amino acid and the like) include alanine, glycine, glycylglycine, aminobutyric acid, N-acetylglycine, N-(tert-butoxycarbonyl)glycine, proline, trans-4-hydroxy-L-proline, phenylalanine, sarcocine, hydantoic acid, creatine, creatine hydrate and N-[tris(hydroxymethy)methyl]glycine Of those, examples of more preferred monocarboxylic acid include tetrahydrofuran-2-carboxylic acid, 2-furancarboxylic acid, 2-pyridinecarboxylic acid, pyroglutamic acid, N-[tris(hydroxymethyl)methyl]glycine, N-acetylglycine, N-(tert-butoxycarbonyl)glycine, creatine hydrate, 2-hydroxyisobutyric acid, glyceric acid, 2,2-bis(hydroxymethyl)propionic acid and 2,2-bis(hydroxymethyl)butyric acid.

Of those, examples of the particularly preferred monocarboxylic acid include tetrahydrofuran-2-carboxylic acid, pyroglutamic acid, N-acetylglycine, 2-hydroxyisobutyric acid, 2,2-bis(hydroxymethyl)propionic acid and 2,2-bis(hydroxymethyl)butyric acid.

Of the above monocarboxylic acids, monocarboxylic acid having a heterocycle containing only an oxygen atom as a heteroatom is preferred, and tetrahydrofuran-2-carboxylic acid is particularly preferred, from the standpoint that when used together with the metal oxide particles and nonionic polymer (P) in a predetermined pH range, a removal rate to a silicon nitride film is suppressed low while maintaining sufficiently high removal rate to a silicon oxide film and high selection ratio between silicon oxide film and silicon nitride film is obtained. The organic acid having a monodentate ligand may be used alone and may be used as mixtures of two or more thereof.

The organic acid having a monodentate ligand represented by the monocarboxylic acid can be used in a form of a salt. Examples of the salt include an ammonium salt, a quaternary ammonium salt, alkali metal salt such as a potassium salt, and an organic amine salt.

The content ratio (concentration) of the organic acid having a monodentate ligand is preferably from 0.003 to 1.0 mass % based on the total mass of the polishing agent. When the content ratio of the organic acid having a monodentate ligand is within the above range, the effect of improving a removal rate to a silicon oxide film and the effect of improving a selection ratio are sufficiently obtained, and dispersion stability of the metal oxide particles as abrasives for polishing is satisfactory. The content ratio of the organic acid having a monodentate ligand is preferably from 0.003 to 1.0 mass %, and more preferably from 0.04 to 0.80 mass %, based on the total mass of the polishing agent.

Nonionic Polymer (P)

The nonionic polymer (P) contained in the polishing agent of the present invention includes at least one selected from the group consisting of polyglycerin, polyoxyethylene polyglyceryl ether and polyoxyoropylene polyglyceryl ether. The nonionic polymer (P) may include only one of those, and may include two or more thereof.

Polyglycerin is a polymer of glycerin in which two or more glycerins have been polymerized. Polyoxyethylene polyglyceryl ether is a compound obtained by addition-polymerizing ethylene oxide with polyglycerin, and polyoxypropylene polyglyceryl ether is a compound obtained by addition-polymerizing propylene oxide with polyglycerin. The degree of polymerization of polyglycerin as a starting material for polyoxyethylene polyglyceryl ether and polyoxypropylene polyglyceryl ether is not particularly limited, and is preferably from 2 to 10, and particularly preferably 2. Specifically, the polyoxyethylene polyglyceryl ether and polyoxypropylene polyglyceryl ether are preferably polyoxyethylene diglyceryl ether and polyoxypropylene diglyceryl ether, respectively.

The nonionic polymer (P) has a weight average molecular weight of preferably from 300 to 100,000, and more preferably from 300 to 10,000. When the weight average molecular weight is 300 or more, the state that the organic acid having a monodentate ligand has adsorbed on the surface of the metal oxide particles and the surface to be polished including the silicon oxide film can be stably obtained. The weight average molecular weight of 100,000 or less is advantageous in handling properties.

Of the nonionic polymers (P), a polymer represented by the following formula (1) (hereinafter referred to as "polymer (1)") is preferred as polyglycerin. A polymer represented by the following formula (2) (hereinafter referred to as "polymer (2)") is preferred as polyoxyethylene polyglyceryl ether. A polymer represented by the following formula (3) (hereinafter referred to as "polymer (3)") is preferred as polyoxypropylene polyglyceryl ether. The nonionic polymer (P) may include at least one selected from the polymer (1), polymer (2) and polymer (3), and may include two or more thereof.

the viewpoint of the handling properties. The weight average molecular weight of the polymer is more preferably from 300 to 10,000.

In the formula (2), $p1+q1+r1+s1$ that is the total of repeating units in four oxyethylene chains is 4 or more, and individual numerical value of p1, q1 r1 and s1 is not limited so long as the total is 4 or more. $p1+q1+r1+s1$ means that $p1+q1+r1+s1$ is 4 or more as an average value among molecules. The upper limit of $p1+q1+r1+s1$ is a numerical value giving a weight average molecular weight of the upper limit.

The polymer (3) is polyoxypropylene diglyceryl ether obtained by addition-polymerizing propylene oxide with diglycerin. The polymer (3) preferably has a weight average molecular weight of 400 or more. When the weight average

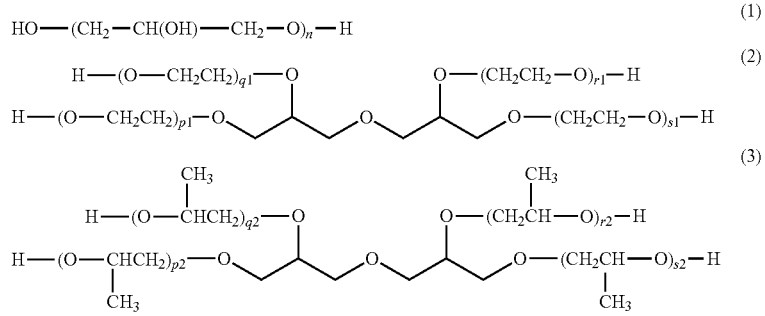

in which $n \geq 4$ in the formula (1), $p1+q1+r1+s1 \geq 4$ in the formula (2), and $p2+q2+r2+s2 \geq 4$ in the formula (3).

Preferred embodiments of the polymers (1) to (3) are described below, but the nonionic polymer (P) is not limited to those embodiments.

The polymer (1) is polyglycerin having a degree of polymerization represented by n of 4 or more. The polymer (1) is preferably polyglycerin having a weight average molecular weight of 300 or more. When the weight average molecular weight is 300 or more, the state that the organic acid having a monodentate ligand has adsorbed on the surface of the metal oxide particles and the surface to be polished which includes a surface including silicon oxide film can be stably obtained. The upper limit of the weight average molecular weight of the polymer (1) is preferably about 100,000 from the standpoint of handling properties and the like. The weight average molecular weight of the polymer (1) is more preferably from 300 to 10,000.

n in the formula (1) is an average value among molecules. The n is 4 or more in average, and the upper limit of n is a numerical value giving a weight average molecular weight of the upper limit. Unless otherwise indicated, the weight average molecular weight in the present specification is a weight average molecular weight measured by gel permeation chromatograph (GPC).

The polymer (2) is polyoxyethylene diglyceryl ether obtained by addition-polymerizing ethylene oxide with diglycerin. The polymer (2) preferably has a weight average molecular weight of 300 or more. When the weight average molecular weight is 300 or more, the state that the organic acid having a monodentate ligand has adsorbed on the surface of the metal oxide particles and the surface to be polished including the silicon oxide film can be stably obtained. The upper limit of the weight average molecular weight of the polymer (2) is preferably about 100,000 from molecular weight is 400 or more, the state that the organic acid having a monodentate ligand is adsorbed on the surface of the metal oxide particles and the surface to be polished including the silicon oxide film can be stably obtained. The upper limit of the polymer (3) is preferably about 100,000 from the standpoint of handling properties and the like. The weight average molecular weight of the polymer (3) is more preferably from 400 to 10,000.

In the formula (3), $p2+q2+r2+s2$ that is the total of repeating units in four oxypropylene chains is 4 or more, and individual numerical value of p2, q2, r2 and s2 is not limited so long as the total is 4 or more. $p2+q2+r2+s24$ means that $p2+q2+r2+s2$ is 4 or more as an average value among molecules. The upper limit of $p2+q2+r2+s2$ is a numerical value giving a weight average molecular weight of the upper limit.

Regarding the commercially available products of the polymers (1) to (3), examples of the polymer (1) include Polyglycerin #310, Polyglycerin #500 and Polyglycerin #750, manufactured by Sakamoto Yakuhin Kogyo Co., Ltd. Example of the polymer (2) includes polyoxyethylene diglyceryl ether having a weight average molecular weight of from 750 to 2,000 in which $p1+q1+r1+s1$ is from 13 to 40, as "SC-E Series" (trade name, manufactured by Sakamoto Yakuhin Kogyo Co., Ltd.). Example of the polymer (3) includes polypropylene diglyceryl ether having a weight average molecular weight of from 750 to 1,600 in which $p2+q2+r2+s2$ is from 9 to 24, as "SC-P Series" (trade name, manufactured by Sakamoto Yakuhin Kogyo Co., Ltd.).

The nonionic polymer (P) may include only at least one selected from polyglycerin, polyoxyethylene polyglyceryl ether and polyoxypropylene polyglyceryl ether, particularly may include only at least one selected from the polymer (1), the polymer (2) and the polymer (3), and may further include a nonionic polymer other than the nonionic polymer (P), in a range that the effect of the present invention is not impaired. The nonionic polymer (P) is preferably constituted of only at least one selected from polyglycerin, polyoxyethylene polyglyceryl ether and polyoxypropylene polyglyceryl ether, particularly only at least one selected from the polymer (1), the polymer (2) and the polymer (3).

The content ratio (concentration) of the nonionic polymer (P) is preferably from 0.0002 to 2.0 mass % based on the total mass of the polishing agent. When the content of the nonionic polymer (P) is from 0.0002 to 2.0 mass %, sufficiently high removal rate to a silicon oxide film is obtained and additionally high selection ratio is obtained. Furthermore, flatness in a pattern is satisfactory. The content ratio of the nonionic polymer (P) is preferably from 0.0005 to 1.0 mass %, and more preferably from 0.001 to 0.80 mass %, based on the total mass of the polishing agent.

pH

The polishing agent of the present invention has a pH of from 3.0 to 7.0. When the pH of the polishing agent is from 3.0 to 7.0, the effect of improvement in removal rate to a silicon oxide film is sufficiently achieved, and dispersion stability of metal oxide particles as abrasives for polishing is satisfactory. The pH of the polishing agent is more preferably from 3.0 to 5.0, and particularly preferably from 3.0 to 4.5.

The polishing agent of the present invention may further include various inorganic acids, inorganic acid salts or basic compounds as a pH regulator in order to adjust the pH thereof to a predetermined value of from 3.0 to 7.0. The inorganic acids or inorganic acid salts are not particularly limited, and, for example, nitric acid, sulfuric acid, hydrochloric acid, phosphoric acid, and their ammonium salts or potassium salts can be used. It is preferred that the basic compound is water-soluble, but the basic acid is not particularly limited to be water-soluble. Examples of the basic compound that can be used include ammonia, potassium hydroxide, quaternary ammonium hydroxide such as tetramethylammonium hydroxide (hereinafter referred to as TMAH) and tetraethylammonium hydroxide, and organic amine such as monoethanolamine and ethylene diamine.

The polishing agent of the present invention can further include a dispersant (or aggregation preventing agent) other than the above components. The dispersant is contained to stably disperse metal oxide particles such as cerium oxide particles in a dispersion medium such as pure water. Examples of the dispersant include anionic, cationic and amphoteric surfactants, and anionic, cationic and amphoteric polymer compounds, and at least one of those dispersants can be contained in the polishing agent of the present invention. Furthermore, the polishing agent of the present invention can appropriately contain a lubricant, a thickener or a viscosity regulator, a preservative and the like as necessary.

The polishing agent of the present invention may be prepared and used such that for the convenience of storage and transportation, a dispersion of metal oxide particles (hereinafter referred as a dispersion α) and an aqueous solution obtained by dissolving the organic acid having a monodentate ligand and the nonionic polymer (P) in water (hereinafter referred to as an aqueous solution β) are separately prepared as two liquids preferably such that each liquid has a pH of from 3.0 to 7.0, and those liquids are mixed when using. The aqueous solution β is a liquid additive for polishing described below.

Liquid Additive for Polishing

The liquid additive for polishing of the present invention is a liquid additive for preparing a polishing agent by mixing with a dispersion of metal oxide particles (the dispersion α described above), includes an organic acid having a monodentate ligand, a nonionic polymer (the nonionic polymer (P)) containing at least one selected from the group consisting of polyglycerin, polyoxyethylene polyglyceryl ether and polyoxypropylene polyglyceryl ether, and water, and has a pH of from 3.0 to 7.0. When the liquid additive for polishing is used in the preparation of a polishing agent, convenience of storage and transportation of a polishing agent can be improved.

Each component of the organic acid having a monodentate ligand, the nonionic polymer (P) and water and the pH of the liquid, in the liquid additive for polishing of the present invention are the same as those described for the polishing agent.

In the liquid additive for polishing of the present invention, the content ratio (concentration) of the organic acid having a monodentate ligand is not particularly limited. However, from the standpoints of easy handling of a liquid additive and easy mixing with a dispersion of metal oxide particles, the content ratio thereof is preferably from 0.003 to 10 mass % based on the total amount of the liquid additive.

In the liquid additive for polishing of the present invention, the content ratio (concentration) of the nonionic polymer (P) is not particularly limited. However, from the standpoints of easy handling of a liquid additive and easy mixing with a dispersion of metal oxide particles, the content ratio thereof is preferably from 0.0002 to 10 mass % based on the total amount of the liquid additive.

The liquid additive for polishing of the present invention has a pH of from 3.0 to 7.0. When the pH of the liquid additive for polishing is from 3.0 to 7.0, by mixing with the dispersion of metal oxide particles, the effects of improvement in removal rate to a silicon oxide film, improvement in flatness in the polishing of a pattern substrate, and the like are sufficiently obtained, and additionally, a polishing agent having satisfactory dispersion stability of metal oxide particles as abrasives for polishing is obtained. The pH of the liquid additive for polishing is more preferably from 3.0 to 5.0, and particularly preferably from 3.0 to 4.5.

In the dispersion of metal oxide particles to be mixed with the liquid additive for polishing, the content ratio (concentration) of the metal oxide particles in the dispersion is preferably from 0.01 to 40 mass % from the standpoint of dispersibility of metal oxide particles and easy handling of the dispersion. The content ratio thereof is more preferably from 0.01 to 20 mass %, and particularly preferably from 0.01 to 10 mass %.

When the liquid additive for polishing of the present invention is mixed with the dispersion of metal oxide particles, the polishing agent having improved removal rate can be achieved while maintaining sufficiently high flatness to a silicon oxide film. In mixing the liquid additive for polishing with the dispersion of metal oxide particles, the liquid additive for polishing may be added to and mixed with the dispersion of metal oxide particles, and the dispersion of metal oxide particles may be added to and mixed with the liquid additive for polishing.

The mixing ratio between the liquid additive for polishing and the dispersion of metal oxide particles is not particularly limited, and the mixing ratio that the content ratios (concentrations) of the organic acid having a monodentate ligand and nonionic polymer (P) are from 0.003 to 1.0 mass % and from 0.0002 to 2.0 mass % based on the total mass of the polishing agent, respectively, in the polishing agent after mixing is preferred. It is preferred that the liquid additive for polishing and the dispersion of metal oxide particles are mixed with each other in a mass ratio of liquid additive for polishing:dispersion of metal oxide particles=130:1 to 1:130 from the standpoint of easy mixing of those.

When the dispersion of metal oxide particles (dispersion α) and the liquid additive for polishing (aqueous solution β) of the present invention are separately prepared as two liquids, and those are mixed with each other to prepare the polishing agent, those liquids are prepared such that the content ratio (concentration) of metal oxide particles in the dispersion α and each concentration of the organic acid having a monodentate ligand and nonionic polymer (P) in the liquid additive for polishing (aqueous solution β) are concentrated to a concentration of from 2 to 100 times the concentration when used as a polishing agent, those liquids thus concentrated are mixed with each other, and the resulting mixture is diluted when used as a polishing agent to achieve a given concentration. More specifically, for example, in case where the dispersion α and the liquid additive for polishing are prepared such that the concentration of metal oxide particles in the dispersion α and each concentration of the organic acid having a monodentate ligand and nonionic polymer (P) in the liquid additive for polishing are 10 times, the dispersion α, the liquid additive for polishing and water are mixed in the proportions of 10 parts by mass, 10 parts by mass and 80 parts by mass, respectively, and the resulting mixture is diluted to 10 times, thereby obtaining a polishing agent.

Preparation Method of Polishing Agent

To prepare the polishing agent of the present invention, for example, a method of adding the organic acid having a monodentate ligand and the nonionic polymer (P) to the dispersion obtained by dispersing the metal oxide particles in water such as pure water or ion-exchanged water, followed by mixing is used. The polishing agent can be preferably prepared such that the pH is within the predetermined range by only the above components. However, in case where the pH is not within the predetermined range, a pH regulator is further added to adjust a pH of the polishing agent obtained such that the pH is within the predetermined range. Uniform polishing agent can be obtained by stirring the polishing agent for a predetermined period of time using a stirrer or the like after the mixing. Furthermore, further satisfactory dispersion state can be obtained by using an ultrasonic disperser after the mixing.

The polishing agent of the present invention is not always required to be provided in the polishing site as a mixture obtained by previously mixing all of polishing components for constituting a polishing agent. The polishing agent may have a desired composition having polishing components mixed, when providing in the polishing site.

Regarding the polishing agent of the present invention, for the convenience of storage and transportation, the dispersion of metal oxide particles (dispersion α) and the liquid additive for polishing (aqueous solution β) are separately prepared as two liquids, and those may be mixed when using. In the case of separating into two liquids of the dispersion α and the aqueous solution β and mixing those to prepare the polishing agent, the concentrations of the organic acid having a monodentate ligand and nonionic polymer (P) in the aqueous solution β are concentrated into, for example, 10 times the concentrations when using the polishing agent, and the aqueous solution β may be diluted with water to obtain predetermined concentrations after mixing, and then used.

Polishing Method

The polishing method according to an embodiment of the present invention is a polishing method including bringing a polishing pad into contact with a surface to be polished of an object to be polished while supplying the polishing agent described above to perform the polishing by relative movement therebetween. The surface to be polished on which the polishing is performed is, for example, a surface which includes a surface including silicon dioxide of a semiconductor substrate. As the semiconductor substrate, the substrate for STI described above is exemplified as a preferred example. The polishing method of the present invention is also effective in the polishing for flattening an interlayer insulating film between multilayer wirings in the manufacturing of a semiconductor device.

The silicon dioxide film in a substrate for STI includes a so-called PE-TEOS film obtained by film formation with a plasma CVD method using tetraethoxysilane (TEOS) as a raw material. The silicon dioxide film further includes a so-called HDP film obtained by film formation with a high density plasma CVD method. The silicon nitride film includes a film obtained by film formation with a low pressure CVD method or a plasma CVD method using silane or dichlorosilane, and ammonia as raw materials.

High flattening can be achieved by performing the polishing by the above-described method using the polishing agent of the present invention. The evaluation of flatness is conducted using, for example, a pattern wafer for STI. The polishing of a pattern for STI is desirably stopped at the time that the silicon nitride film has been exposed, and it is advantageous for flatness as the silicon nitride film of a pattern wafer is not shaved. Therefore, the decreased amount of a film thickness of the silicon nitride film can be used as an index of flatness. The index means that flatness is improved as the decreased amount of a film thickness of the silicon nitride film decreases.

Figure 2:
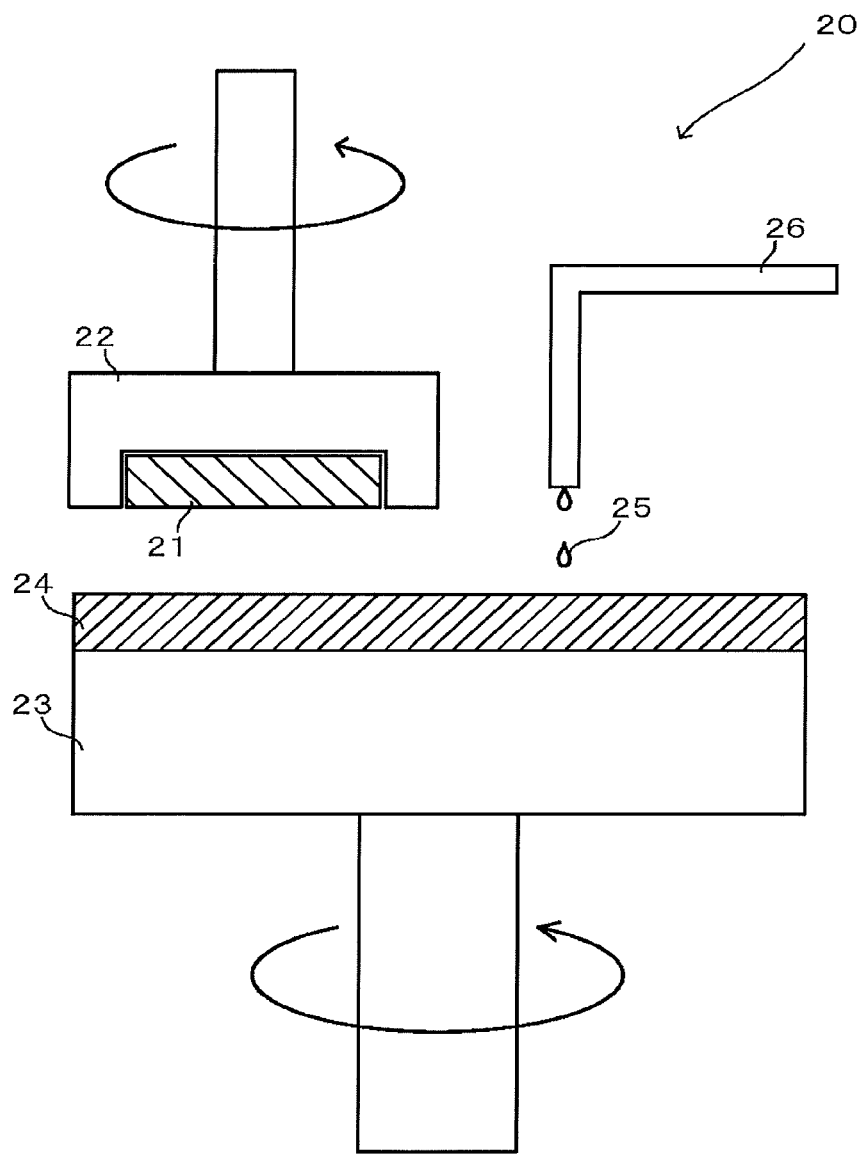
FIG. 2 is a view showing one example of a polishing machine usable in the polishing method of the present invention.

In the polishing method according to the embodiment of the present invention, the conventional polishing machine can be used. FIG. 2 is a view showing one example of a polishing machine usable in the polishing method of the present invention.

This polishing machine 20 includes a polishing head 22 for holding a semiconductor substrate 21 such as an STI substrate, a polishing platen 23, a polishing pad 24 stuck onto the surface of the polishing platen 23, and a polishing agent supply tube 26 for supplying a polishing agent 25 to the polishing pad 24. The polishing machine is constituted such that the surface to be polished of the semiconductor substrate 21 held by the polishing head 22 is brought into contact with the polishing pad 24 while supplying the polishing agent 25 from the polishing agent supply tube 26, and the polishing head 22 and the polishing platen 23 are relatively rotated to perform polishing. The polishing machine used in the embodiment of the present invention is not limited to this structure.

The polishing head 22 may perform not only rotation movement, but also linear movement. The polishing platen 23 and the polishing pad 24 may have a size equivalent to or smaller than the size of the semiconductor substrate 21. In this case, it is preferred to relatively move the polishing head 22 and the polishing platen 23, thereby making it possible to polish the entire surface of the surface to be polished of the semiconductor substrate 21. The polishing platen 23 and the polishing pad 24 may not perform rotation movement, but may move, for example, in one direction by a belt system.

The polishing conditions of the polishing machine 20 are not particularly limited. However, polishing pressure is increased by applying a load to the polishing head 22 to press the polishing head to the polishing pad 24, and, as a result, removal rate can be improved. The polishing pressure is preferably from about 0.5 to 50 kPa, and from the standpoints of uniformity of the removal rate in the surface to be polished of the semiconductor substrate 21, flatness and prevention of polishing defects such as scratches, the polishing pressure is more preferably from about 3 to 40 kPa. The number of rotations of the polishing platen 23 and the polishing head 22 is preferably from about 50 to 500 rpm, but is not limited to this range. The supply amount of the polishing agent 25 is appropriately adjusted by a composition of the polishing agent, polishing conditions described above, and the like.

As the polishing pad 24, a pad including a nonwoven fabric, a foamed polyurethane, a porous resin, a non-porous resin or the like may be used. To accelerate the supply of the polishing agent 25 to the polishing pad 24 or to allow a certain amount of the polishing agent 25 to stay in the polishing pad 24, groove processing such as a lattice shape, a concentric shape or a helical shape may be applied to the surface of the polishing pad 24. Furthermore, as necessary, a pad conditioner may be brought into contact with the surface of the polishing pad 24, and the polishing may be performed while conditioning the surface of the polishing pad 24.

According to the polishing method of the present invention, in CMP treatment such as flattening of an interlayer insulating film or flattening of an insulating film for STI in the manufacturing of a semiconductor device, the surface to be polished including silicon oxide (for example, silicon dioxide) can be polished in high removal rate. Additionally, high selection ratio between a silicon oxide film and a silicon nitride film is realized, and high flatness can be achieved.

EXAMPLES

The present invention is specifically described below by reference to working examples and comparative examples, but the invention should not be construed as being limited to those examples.

Examples 1 to 15 are working examples, and Examples 16 to 20 are comparative examples. In the following examples, unless otherwise indicated, "%" means "mass %". Characteristic values were measured and evaluated by the following methods.
pH The pH was measured using a pH meter MH-30R manufactured by DKK-TOA Corporation.
Average Secondary Particle Size The average secondary particle size was measured using a laser diffraction/scattering particle size distribution analyzer (manufactured by Horiba, Ltd., device name: LA-920).
Polishing Characteristics The polishing characteristics were evaluated by performing polishing using a fully automatic CMP polishing device (manufactured by Applied Materials, device name: Mirra). Two-layer pad (VP-3100 manufactured by Dow) was used as the polishing pad, and CVD diamond pad conditioner (manufactured by 3M, trade name: Trizact B5) was used for conditioning the polishing pad. The polishing conditions were polishing pressure: 21 kPa, the number of rotations of polishing platen: 77 rpm, and the number of rotations of polishing head: 73 rpm. Furthermore, the supply rate of the polishing agent was 200 ml/min.

For the measurement of a removal rate, a silicon dioxide film-attached blanket substrate in which a silicon dioxide film has been formed on an 8-inch silicon wafer by plasma CVD using tetraethoxysilane as a raw material and a silicon nitride film-attached blanket substrate in which a silicon nitride film has been formed on an 8-inch silicon wafer by CVD were used as a polishing object (an object to be polished).

A film thickness meter UV-1280SE manufactured by KLA-Tencor was used for the measurement of film thicknesses of the silicon dioxide film and silicon nitride film formed on the respective blanket substrates. The removal rates to the silicon dioxide film and the silicon nitride film were calculated by obtaining the difference between the film thickness of the blanket substrate before polishing and the film thickness thereof after polishing for 1 minute, respectively. An average value (angstrom/min) of the removal rate obtained from removal rates at 49 places on the surface of the substrate was used as evaluation index of removal rate. Furthermore, the ratio between a removal rate of a silicon dioxide film and a removal rate of a silicon nitride film (removal rate of silicon dioxide film/removal rate of silicon nitride film) was calculated as a selection ratio.

Example 1

A cerium oxide dispersion (hereinafter referred to as cerium oxide dispersion a) obtained by dispersing cerium oxide particles having an average secondary particle size of 120 nm in pure water was added to pure water such that the content ratio (concentration) of the cerium oxide particles was 0.25% based on the total mass of a polishing agent, and tetrahydrofuran-2-carboxylic acid (hereinafter referred to as "THF-C") as an organic acid having a monodentate ligand and polyoxyethylene diglyceryl ether (trade name: SC-E750, manufactured by Sakamoto Yakuhin Kogyo Co., Ltd., p1+q1+r1+s1=about 13 in the formula (2), weight average molecular weight: 750) (hereinafter referred to as nonionic polymer A. Shown as "Polyoxyethylene diglyceryl ether (Mw 750)" in Table 1. Mw means a weight average molecular weight.) as a polymer (2) were then added to the dispersion such that the content ratio (concentration) of THF-C was 0.10% and the content ratio (concentration) of the nonionic polymer A was 0.010%, followed by stirring. Monoethanolamine (hereinafter referred to as MEA) was further added to the resulting mixture to adjust its pH to 3.5. Thus, a polishing agent (1) was obtained.

Examples 2 to 8

The same cerium oxide dispersion a, tetrahydrofuran-2-carboxylic acid and nonionic polymer A as used in Example 1 were added to pure water such that their content ratios (concentrations) were the content ratios (concentrations) shown in Table 1, respectively, followed by stirring. MEA was further added to the respective resulting mixtures to adjust their pH to the respective pH shown in Table 1. Thus, polishing agents (2) to (9) were obtained.

Example 10

The same cerium oxide dispersion a and tetrahydrofuran-2-carboxylic acid as used in Example 1 and polyglycerin (trade name: Polyglycerin #310, manufactured by Sakamoto Yakuhin Kogyo Co., weight average molecular weight: 310) (hereinafter referred to as nonionic polymer B. Shown as "Polyglyceryin (Mw 310) in Table 1) as a polymer (1) were added to pure water such that their content ratios (concentrations) were the content ratios (concentrations) shown in Table 1, respectively, followed by stirring. MEA was further added to the resulting mixture to adjust its pH to the pH shown in Table 1. Thus, polishing agent (10) was obtained.

Example 11

The same cerium oxide dispersion a and tetrahydrofuran-2-carboxylic acid as used in Example 1 and polyoxypropylene diglyceryl ether (trade name: SC-P400, manufactured by Sakamoto Yakuhin Kogyo Co., p2+q2+r2+s2=about 4 in the formula (3), weight average molecular weight: 400) (hereinafter referred to as nonionic polymer C. Shown as "Polyoxypropylene diglyceryl ether (Mw 400) in Table 1) as a polymer (3) were added to pure water such that their content ratios (concentrations) were the content ratios (concentrations) shown in Table 1, respectively, followed by stirring. MEA was further added to the resulting mixture to adjust its pH to the pH shown in Table 1. Thus, polishing agent (11) was obtained.

Example 12

A cerium oxide dispersion (hereinafter referred to as cerium oxide dispersion b) obtained by dispersing cerium oxide particles having an average secondary particle size of 100 nm in pure water was added to pure water such that the content ratio (concentration) of the cerium oxide particles was 0.25% based on the total mass of a polishing agent, and tetrahydrofuran-2-carboxylic acid and polyoxyethylene diglyceryl ether (trade name: SC-E1000, manufactured by Sakamoto Yakuhin Kogyo Co., Ltd., p1+q1+r1+s1=about 20 in the formula (2), weight average molecular weight: 1000) (hereinafter referred to as nonionic polymer D. Shown as "Polyoxyethylene diglyceryl ether (Mw 1000) in Table 1) as a polymer (2) were then added to the pure water such that their content ratios (concentrations) were the content ratios (concentrations) shown in Table 1, respectively, followed by stirring. MEA was further added to the resulting mixture to adjust its pH to the pH shown in Table 1. Thus, a polishing agent (12) was obtained.

Example 13

The same cerium oxide dispersion a as used in Example 1, N-acetylglycine as an organic acid having a monodentate ligand and the nonionic polymer A were added to pure water such that their content ratios (concentrations) were the content ratios (concentrations) shown in Table 1, respectively, followed by stirring. MEA was further added to the resulting mixture to adjust its pH to the pH shown in Table 1. Thus, a polishing agent (13) was obtained.

Example 14

A cerium oxide dispersion (hereinafter referred to as cerium oxide dispersion c) obtained by dispersing cerium oxide particles having an average secondary particle size of 170 nm in pure water was added to pure water such that the content ratio (concentration) of the cerium oxide particles was 0.25% based on the total mass of a polishing agent, and 2,2-bis(hydroxymethyl)propionic acid as an organic acid having a monodentate ligand and the nonionic polymer A were then added to the pure such that their content ratios (concentrations) were the content ratios (concentrations) shown in Table 1, respectively, followed by stirring. MEA was further added to the resulting mixture to adjust its pH to the pH shown in Table 1. Thus, a polishing agent (14) was obtained.

Example 15

The same cerium oxide dispersion c as used in Example 14, DL-pyroglutamic acid as an organic acid having a monodentate ligand, and the nonionic polymer A were added to pure water such that their content ratios (concentrations) were the content ratios (concentrations) shown in Table 1, respectively, followed by stirring. MEA was further added to the resulting mixture to adjust its pH to the pH shown in Table 1. Thus, a polishing agent (15) was obtained.

Example 16

The same cerium oxide dispersion a and tetrahydrofuran-2-carboxylic acid as used in Example 1, and polyvinyl alcohol (a nonionic polymer that is not the nonionic polymer (P)) were added to pure water such that their content ratios (concentrations) were the content ratios (concentrations) shown in Table 1, respectively, followed by stirring. MEA was further added to the resulting mixture to adjust its pH to the pH shown in Table 1. Thus, a polishing agent (16) was obtained.

Example 17

The same cerium oxide dispersion c as used in Example 14, and DL-pyroglutamic acid were added to pure water such that their content ratios (concentrations) were the content ratios (concentrations) shown in Table 1, respectively, followed by stirring. MEA was further added to the resulting mixture to adjust its pH to the pH shown in Table 1. Thus, a polishing agent (17) was obtained.

Example 18

The same cerium oxide dispersion a and tetrahydrofuran-2-carboxylic acid as used in Example 1 were added to pure water such that their content ratios (concentrations) were the content ratios (concentrations) shown in Table 1, respectively, followed by stirring. MEA was further added to the resulting mixture to adjust its pH to the pH shown in Table 1. Thus, a polishing agent (18) was obtained.

Example 19

The same cerium oxide dispersion α, tetrahydrofuran-2-carboxylic acid and nonionic polymer A as used in Example 1 were added to pure water such that their content ratios (concentrations) were the content ratios (concentrations) shown in Table 1, respectively, followed by stirring. MEA was further added to the resulting mixture to adjust its pH to the pH (pH in a range outside the range of the polishing agent of the present invention) shown in Table 1. Thus, a polishing agent (19) was obtained.

Example 20

The same cerium oxide dispersion a as used in Example 1, polyacrylic acid as an organic acid that is not an organic acid having a monodentate ligand and the nonionic polymer A were added to pure water such that their content ratios (concentrations) were the content ratios (concentrations) shown in Table 1, respectively, followed by stirring. Nitric acid was further added to the resulting mixture to adjust its pH to the pH shown in Table 1. Thus, a polishing agent (20) was obtained.

Polishing characteristics (removal rate to a silicon dioxide film, removal rate to a silicon nitride film, and selection ratio) of the polishing agents (1) to (20) obtained in Examples 1 to 20 were measured by the above respective methods. The measurement results are shown in Table 1.

TABLE 1

| Example | Average secondary particle size of cerium oxide (nm) | Concentration of cerium oxide (mass %) | Organic acid | Concentration of organic acid (mass %) | Nonionic polymer | Concentration of nonionic polymer (mass %) | pH | Removal rate to silicon oxide film (Angstrom/min) | Removal rate to silicon nitride film (Angstrom/min) | Selection ratio |
|---|---|---|---|---|---|---|---|---|---|---|
| 1 | 120 | 0.25 | THF-C | 0.10 | Polyoxyethylene diglyceryl ether (Mw 750) | 0.010 | 3.5 | 3669 | 3.9 | 948 |
| 2 | 120 | 0.25 | THF-C | 0.10 | Polyoxyethylene diglyceryl ether (Mw 750) | 0.0010 | 3.5 | 3282 | 2.0 | 1641 |
| 3 | 120 | 0.25 | THF-C | 0.10 | Polyoxyethylene diglyceryl ether (Mw 750) | 0.0005 | 3.5 | 2903 | 4.0 | 726 |
| 4 | 120 | 0.25 | THF-C | 0.10 | Polyoxyethylene diglyceryl ether (Mw 750) | 0.200 | 3.5 | 3662 | 3.5 | 1034 |
| 5 | 120 | 0.25 | THF-C | 0.10 | Polyoxyethylene diglyceryl ether (Mw 750) | 1.000 | 3.5 | 3052 | 4.3 | 710 |
| 6 | 120 | 0.25 | THF-C | 0.040 | Polyoxyethylene diglyceryl ether (Mw 750) | 0.010 | 4.5 | 4668 | 5.0 | 934 |
| 7 | 120 | 0.25 | THF-C | 0.06 | Polyoxyethylene diglyceryl ether (Mw 750) | 0.010 | 3.0 | 1041 | 1.9 | 555 |
| 8 | 120 | 0.25 | THF-C | 0.20 | Polyoxyethylene diglyceryl ether (Mw 750) | 0.010 | 3.5 | 3145 | 3.7 | 841 |
| 9 | 120 | 0.025 | THF-C | 0.10 | Polyoxyethylene diglyceryl ether (Mw 750) | 0.010 | 3.5 | 1007 | 2.0 | 504 |
| 10 | 120 | 0.25 | THF-C | 0.10 | Polyglycerin (Mw 310) | 0.100 | 3.5 | 3301 | 2.4 | 1381 |
| 11 | 120 | 0.25 | THF-C | 0.10 | Polyoxypropylene diglyceryl ether (Mw 400) | 0.010 | 3.5 | 3288 | 2.4 | 1351 |
| 12 | 100 | 0.25 | THF-C | 0.10 | Polyoxyethylene diglyceryl ether (Mw 1000) | 0.010 | 3.5 | 2954 | 2.2 | 1341 |
| 13 | 120 | 0.25 | N-acetylglycine | 0.05 | Polyoxyethylene diglyceryl ether (Mw 750) | 0.010 | 3.5 | 3419 | 4.5 | 767 |
| 14 | 170 | 0.25 | 2,2-bis(hydroxymethyl) propionic acid | 0.10 | Polyoxyethylene diglyceryl ether (Mw 750) | 0.010 | 3.5 | 4330 | 14.8 | 292 |
| 15 | 170 | 0.25 | DL-pyroglutamic acid | 0.007 | Polyoxyethylene diglyceryl ether (Mw 750) | 0.010 | 3.5 | 3425 | 3.8 | 895 |
| 16 | 120 | 0.25 | THF-C | 0.10 | Polyvinyl alcohol (PVA) | 0.100 | 3.5 | 115 | 1.7 | 70 |
| 17 | 170 | 0.25 | DL-pyroglutamic acid | 0.20 | — | 0.000 | 3.5 | 286 | 1.8 | 158 |
| 18 | 120 | 0.25 | THF-C | 0.002 | — | 0.000 | 4.5 | 3257 | 320 | 10 |
| 19 | 120 | 0.25 | THF-C | 0.002 | Polyoxyethylene diglyceryl ether (Mw 750) | 0.010 | 8.5 | Impossible to measure due to aggregation | | |
| 20 | 120 | 0.50 | Polyacrylic acid | 0.05 | Polyoxyethylene diglyceryl ether (Mw 750) | 0.010 | 5.0 | 1673 | 43.4 | 39 |

It can be seen from Table 1 that when polishing was performed using the polishing agents (1) to (15) of Examples 1 to 15 each including cerium oxide particles as the metal oxide particles, an organic acid having a monodentate ligand, the nonionic polymer (P) and water and having a pH of from 3.0 to 7.0, high removal rate to a silicon dioxide film is obtained. Furthermore, it can be seen that the selection ratio between a silicon dioxide film and a silicon nitride film becomes extremely high.

On the other hand, it can be seen that when the polishing agent (16) of Example 16 that contains polyvinyl alcohol as a nonionic polymer but does not contain the nonionic polymer (P) and the polishing agent (17) of Example 17 that does not contain a nonionic polymer at all were used, a removal rate to a silicon dioxide film greatly decreases as compared with those of Examples 1 to 15. Furthermore, it can be seen that when the polishing agent (18) that does not contain a nonionic polymer at all and differs from Example 17 in the kind of an organic acid having a monodentate ligand and the polishing agent (20) of Example 20 that contains polyacrylic acid as an organic acid that is not an organic acid having a monodentate ligand were used, the selection ratio between a silicon dioxide film and a silicon nitride film greatly decreases as compared with those of Examples 1 to 15. Furthermore, when the polishing agent (19) of Example 19 in which the pH was adjusted to 8.5 was used, aggregation occurred, and a removal rate could not be evaluated.

The present application is based on Japanese Patent Application No. 2016-178507 filed on Sep. 13, 2016, and the contents are incorporated herein by reference.

According to the present invention, a removal rate to a silicon nitride film can be suppressed low while maintaining sufficiently high removal rate to a silicon oxide film in, for example, CMP of a surface to be polished which includes a surface including silicon oxide, and high selection ratio between a silicon oxide film and a silicon nitride film can be achieved. Therefore, the polishing agent and polishing method of the present invention are suitable for flattening an insulating film for STI in the manufacturing of a semiconductor device.

DESCRIPTION OF REFERENCE NUMERALS AND SIGNS

1: Silicon substrate
2: Silicon nitride film
3: Trench
4: Silicon dioxide film
20: Polishing machine
21: Semiconductor substrate
22: Polishing head
23: Polishing platen
24: Polishing pad 25: Polishing agent
26: Polishing agent supply tube

What is claimed is:

1. A polishing agent comprising:
cerium oxide particles;
an organic acid;
a nonionic polymer; and
water;
wherein:
the polishing agent optionally comprises an inorganic acid or a salt of the inorganic acid, and when the polishing agent comprises the inorganic acid or a salt of the inorganic acid, the inorganic acid is at least one selected from the group consisting of: nitric acid, sulfuric acid, and hydrochloric acid;
the polishing agent has a pH of from 3.0 to 7.0;
the organic acid consists of:
at least one selected from the group consisting of 2-hydroxyisobutyric acid, 2,2-bis(hydroxymethyl)propionic acid, and 2,2-bis(hydroxymethyl)butyric acid;
optionally, a monocarboxylic acid having a heterocycle;
optionally, a monocarboxylic acid having an amino group;
optionally, a monocarboxylic acid having 4 or more carbon atoms and having a hydroxyl group other than 2-hydroxyisobutyric acid, 2,2-bis(hydroxymethyl)propionic acid, or 2,2-bis(hydroxymethyl)butyric acid; and
optionally, a monocarboxylic acid having an amino group; and
the nonionic polymer comprises at least one selected from the group consisting of polyglycerin, polyoxyethylene polyglyceryl ether, and polyoxypropylene polyglyceryl ether.

2. The polishing agent according to claim 1, wherein the monocarboxylic acid is contained in an amount of from 0.003 to 1.0 mass % based on a total mass of the polishing agent.

3. The polishing agent according to claim 1, wherein the nonionic polymer is contained in an amount of from 0.0002 to 2.0 mass % based on a total mass of the polishing agent.

4. The polishing agent according to claim 1, wherein the cerium oxide particles have an average secondary particle size of from 10 nm to 500 nm.

5. The polishing agent according to claim 1, wherein the cerium oxide particles are contained in an amount of from 0.01 to 10.0 mass % based on a total mass of the polishing agent.

6. A polishing method comprising bringing a polishing pad into contact with a surface to be polished while supplying a polishing agent to perform polishing by relative movement therebetween,
wherein the surface to be polished including a surface comprising silicon oxide of a semiconductor substrate is polished using the polishing agent according to claim 1 as the polishing agent.

7. The polishing agent according to claim 1, wherein the organic acid comprises the monocarboxylic acid having a heterocycle, and the heterocycle comprises nitrogen.

8. The polishing agent according to claim 1, wherein the organic acid comprises the monocarboxylic acid having a heterocycle, and the heterocycle comprises a heteroatom other than nitrogen.

9. The polishing agent according to claim 1, wherein the organic acid comprises the monocarboxylic acid having a heterocycle, and the monocarboxylic acid having a heterocycle is tetrahydrofuran-2-carboxylic acid.

10. The polishing agent according to claim 1, wherein the organic acid comprises the monocarboxylic acid having 4 to 10 carbon atoms and having a hydroxyl group other than 2-hydroxyisobutyric acid, 2,2-bis(hydroxymethyl)propionic acid, or 2,2-bis(hydroxymethyl)butyric acid.

11. The polishing agent according to claim 1, wherein the nonionic polymer comprises at least one selected from the group consisting of polyglycerin and polyoxyethylene polyglyceryl ether.

12. The polishing agent according to claim 1, wherein the nonionic polymer has a weight average molecular weight of 300 to 10,000.

13. The polishing agent according to claim 1, wherein the nonionic polymer has a weight average molecular weight of 300 to 1,000.

14. A shallow trench isolation process, comprising applying the polishing agent of claim 1 to a surface comprising silicon oxide during chemical mechanical polishing.

15. The polishing agent according to claim 1, wherein the organic acid comprises the monocarboxylic acid having an amino group, and the monocarboxylic acid having an amino group is N-acetylglycine.

* * * * *